(12) United States Patent
Merget

(10) Patent No.: US 7,847,117 B2
(45) Date of Patent: Dec. 7, 2010

(54) PROCESS FOR PREPARING ALKYL(METHOXYMETHYL) TRIMETHYLSILANYLMETHYLAMINES

(75) Inventor: Markus Merget, Mehring (DE)

(73) Assignee: Wacker Chemie AG, Munich (DE)

( * ) Notice: Subject to any disclaimer, the term of this patent is extended or adjusted under 35 U.S.C. 154(b) by 86 days.

(21) Appl. No.: 12/180,716

(22) Filed: Jul. 28, 2008

(65) Prior Publication Data

US 2009/0036700 A1 Feb. 5, 2009

(30) Foreign Application Priority Data

Aug. 1, 2007 (DE) .................. 10 2007 036 068

(51) Int. Cl.
*C07F 7/04* (2006.01)
(52) U.S. Cl. ..................................... 556/423
(58) Field of Classification Search ............... None
See application file for complete search history.

(56) References Cited

U.S. PATENT DOCUMENTS

| | | | |
|---|---|---|---|
| 6,057,342 A | 5/2000 | Fevig et al. | |
| 6,245,001 B1 | 6/2001 | Siaperas | |
| 6,265,434 B1 | 7/2001 | Caldwell et al. | |
| 7,230,119 B2 * | 6/2007 | Chand et al. | 548/535 |
| 7,419,990 B2 * | 9/2008 | Sings et al. | 514/326 |
| 7,649,002 B2 * | 1/2010 | Calabrese et al. | 514/326 |
| 2009/0093512 A1 * | 4/2009 | O'Neill et al. | 514/292 |

FOREIGN PATENT DOCUMENTS

| | | |
|---|---|---|
| DE | 69921340 T2 | 3/2005 |
| EP | 0398616 A | 11/1990 |
| WO | WO 00/15611 A1 | 3/2000 |
| WO | WO 03/061567 A2 | 7/2003 |
| WO | WO 03/062252 A1 | 7/2003 |
| WO | WO 03061567 A | 7/2003 |
| WO | WO 03062252 A | 7/2003 |
| WO | WO 2005009950 A | 2/2005 |
| WO | WO 2005049602 A | 6/2005 |
| WO | WO 2006040182 A | 4/2006 |

OTHER PUBLICATIONS

Hosomi et al., {Chemistry of organosilicon compounds. 195. N-(Trimethylsilylmethyl)aminomethyl ethers as azomethine ylide synthons. A new and convenient access to pyrrolidine derivatives, Chemistry Letters (1984), (7), 1117-1120}.*
Padwa A. et al., On the Use of N-[ Trimethylsilyl) methyl] ¾ amino Ethers as Capped Azomethine Ylide Equivalents, Journal of Organic Chemistry, American Chemical Society, Easton.: US, vol. 52, No. 2, Jan. 23, 1987, p. 234-244.
Hosomi A. et al., N-(Trimethylsilytmethyl) aminomethyl Ethers as Azomethine Ylide Synthons: a new and Convenient access to Pyrrolidine derivatives, Chemistry Letters, 1984, p. 1117-1120.
Chen et al., Synthesis and characterization of trans-4-(4-chlorophenyl) pyrrolidine 3-carboxamides of piperazinecyclohexanes as ligands for the melanocortin-4 receptor, Bioorganic & Medicinal Chemistry Letters, Pergamon, Elsevier Science, GB, vol. 17, No. 24, Oct. 17, 2007, p. 6825-6831.
Padwa, A. et al., "On the Use of N-[ (Trimethylslsilyl)methyl]amino Ethers as Capped Azomethine Ylide Equivalents," J: Org. Chem., 1987, 52, pp. 235-244.
Kotian, P. et al., "A Practical Large-Scale Synthesis of (3R,4R)-4-(Hydroxymethyl)pyrrolidin-3-ol via Asymmetric 1, 3,-Dipolar Cycloaddition," Org. Process Res. & Dev., 2005, 9, pp. 193-197.
Padwa, A. et al., "N-Benzyl-N-Methoxymethyl-N-(Trimeethylsilyl)Mthylamine as an Azomethine Ylide Eqivalent: 2,6-Dioxo-1-Phenyl-4-Benzyl-1,4-Dizabicyclo[3.3.0]Octane (Pyrrolo[3,4-c]pyrrole-1,3(2H,3aH)-dione, tetrahydro-2-phenyl-5-(phenylmethyl)-, cis-)," Org. Syntheses, 1989, 67, pp. 133-140.

* cited by examiner

*Primary Examiner*—Daniel M Sullivan
*Assistant Examiner*—Chukwuma O Nwaonicha
(74) *Attorney, Agent, or Firm*—Brooks Kushman P.C.

(57) ABSTRACT

Alkyl(methoxymethyl)trimethylsilanylmethylamines are prepared by reacting alkyltrimethylsilanylmethylamines with a substantially equimolar amount of paraformaldehyde and methanol in the presence of a base.

10 Claims, 1 Drawing Sheet

PROCESS FOR PREPARING ALKYL(METHOXYMETHYL) TRIMETHYLSILANYLMETHYLAMINES

BACKGROUND OF THE INVENTION

1. Field of the Invention

The present invention relates to processes for preparing alkyl(methoxymethyl)trimethylsilanylmethylamines.

2. Background Art

The literature describes the syntheses of various alkyl(methoxymethyl)trimethylsilanylmethylamines of the general formula (A).

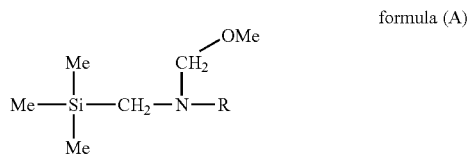

formula (A)

The R radical may be defined, for example, as benzyl, tert-butyl, 2-vinylbenzyl, isopropyl, 2-hydroxy-2-phenylethanoyl, 4-nonylbenzyl, 4-methoxybenzyl, 4-chlorobenzyl, 4-bromobenzyl, allyl, 3-pyridinylmethyl, (R)- and (S)-1-phenylethyl, (S)-1-naphthylethyl, or cyclohexyl.

Alkyl(methoxymethyl)trimethylsilanylmethylamines are used as building blocks for preparing pyrrolidines. In this case, the compounds detailed above are converted in the presence of strong acids, for example trifluoroacetic acid, or Lewis acids such as lithium fluoride, to azomethinylides, which can then react stereoselectively with alkenes by means of 3+2 cycloaddition (reaction scheme (I)) (Review article: A. Padwa, W. Dent, J. ORG. CHEM. 1987, 52, 235-244.).

Reaction scheme (I)

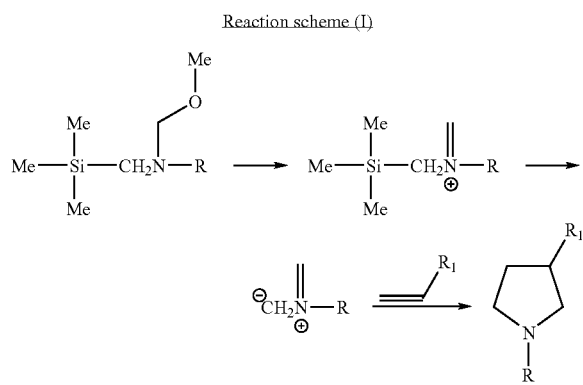

The literature describes two fundamentally different access routes to alkyl(methoxymethyl)trimethylsilanylmethylamines.

WO2000015611 describes a process for preparation proceeding from alkyltrimethylsilanylmethylamines. Deprotonation with a strong base, for example n-butyllithium, converts the compound to the corresponding amide (reaction equation (II)). This is subsequently reacted with chloromethyl methyl ether in a substitution reaction to give the desired target compound. This synthesis has the crucial disadvantage that chloromethyl ethers are highly carcinogenic.

Reaction scheme (II)

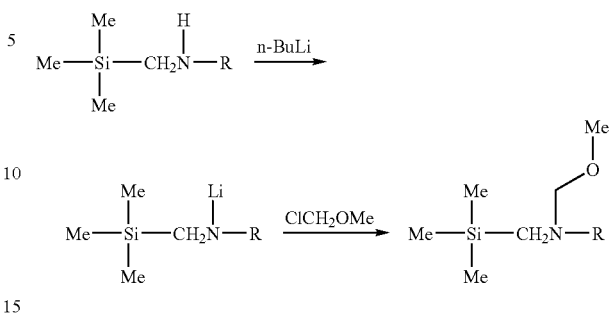

Another means of preparing alkyl(methoxymethyl)trimethylsilanylmethylamines described many times in the literature is the reaction of alkyltrimethylsilanylmethylamines with aqueous formaldehyde solution and methanol in the presence of a base, according to reaction scheme (III).

Reaction scheme (III)

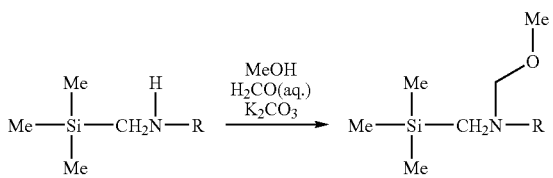

The isolated yields for the different compounds are within the range of 49 and 88%. Often, the target compound is also isolated only as a crude compound and is converted further in situ. In the syntheses, between 1.8 and 56 equivalents of methanol (based on the corresponding alkyltrimethylsilanylmethylamine) and between 1.0 and 2.9 equivalents of formaldehyde (based on the corresponding alkyltrimethylsilanylmethylamine) are used. The formaldehyde is used in the form of an aqueous solution in concentrations between 30 and 38% by weight. The base used is predominantly $K_2CO_3$ (0.04 to 1.2 equivalents); in some cases, NaOH is also used (0.17 to 1.36 equivalents). The reactions are conducted at temperatures around 0° C.

P. Kotian et. al. (ORG. PROCESS RES. DEV. 2005, 9, 193-197), describe the preparation of benzyl(methoxymethyl)trimethylsilanylmethylamines by means of the above-described synthesis. In purifying the benzyl(methoxymethyl)trimethylsilanylmethylamines by distillation on a large scale (batch size 9.14 mol of benzyl-trimethylsilanylmethylamine), however, the product decomposes.

WO-2003062252 and WO-2003061567 both describe, in the examples, identical processes for preparing nonylbenzyl(methoxymethyl)-trimethylsilanylmethylamine. Instead of an aqueous formaldehyde solution, in both cases, paraformaldehyde (2.13 equivalents) is used as the formaldehyde source. The base employed is solid NaOH (0.17 equivalent). In these methods, the target product is not isolated further, but rather processed directly from the crude product, without downstream distillation, which would entail the known problems. Paraformaldehyde is not added in an equimolar amount in the process described.

The literature processes which use an aqueous formaldehyde solution as the formaldehyde source all have the disadvantage that they can be converted to a larger scale only with great problems owing to thermal instabilities. In the processes with paraformaldehyde, the prior art does not suggest any means as to how workup problems can be eliminated.

SUMMARY OF THE INVENTION

It was therefore an object of the invention to provide a process for preparing alkyl(methoxymethyl)trimethylsilanylmethylamines, which affords high yields and purities, the product of which can be isolated by distillation. A further important object was to provide a process which has improved safety with respect to the reaction itself and the product isolation.

DETAILED DESCRIPTION OF THE PREFERRED EMBODIMENT(S)

Figure 1:
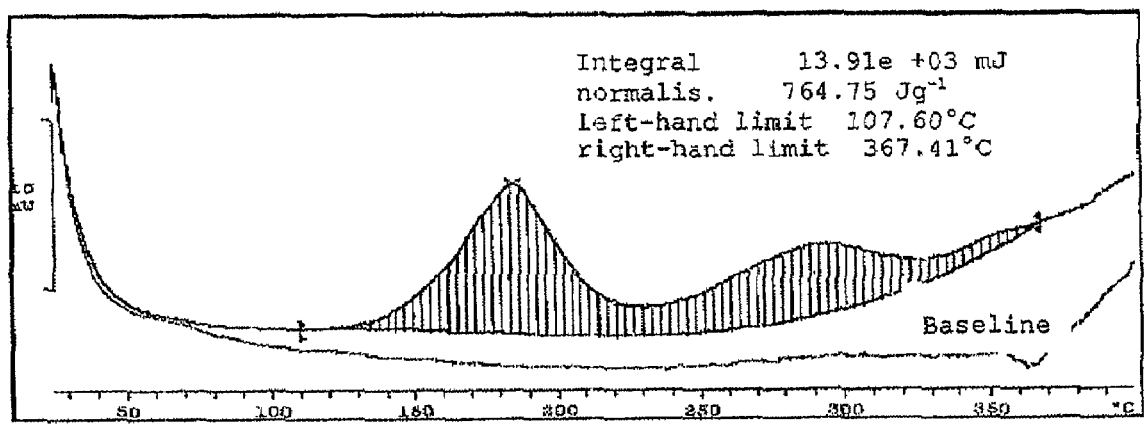
FIG. 1 is a spectrum of a DSC analysis.

The invention thus provides a process for preparing alkyl (methoxymethyl)trimethylsilanylmethylamines by reacting alkyltrimethylsilanylmethylamines with paraformaldehyde and methanol in the presence of a base, which comprises using paraformaldehyde and the appropriate alkyltrimethylsilanylmethylamine in a molar ratio of from 0.8:1.0 to 1.0:0.8.

In the process of the invention, in general, paraformaldehyde, methanol and the base used are initially charged. Subsequently, an alkyl-trimethylsilanylmethylamine is metered thereto. Alkyltrimethylsilanylmethylamines can be prepared by general literature standard methods, for example, A. Padwa, W. Dent, ORG. SYNTHESES 1989, 67, 133-140. After a postreaction time, a solvent, for example pentane, is metered in and the two phases formed are separated. An azeotropic drying is followed by concentration and isolation.

The base employed is preferably $K_2CO_3$, although the use of $Na_2CO_3$, NaOH, NaOMe and/or other bases are also possible. The amount of base is not crucial.

The reaction temperature is in the range between $-20°$ C. and $40°$ C. Preference is given to a reaction temperature of from $-10$ to $110°$ C., more preferably $0°$ C.

The ratio between alkyltrimethylsilanylmethylamine and methanol in the process is not crucial. The ratio is preferably between 1.0 and 2.5 molar equivalents, more preferably from 1.7 to 2.2 molar equivalents and most preferably 1.9 molar equivalents of alkyltrimethylsilanylmethylamine per equivalent of methanol.

The use of paraformaldehyde as the formaldehyde source is crucial for the process. The chain length of the paraformaldehyde is unimportant. Preference is given to using commercially available paraformaldehyde without a defined chain length. Paraformaldehyde and the corresponding alkyltrimethylsilanylmethylamine are preferably used in a molar ratio of from 0.8:1.0 to 1.0:0.8, more preferably 0.9:1.0 to 1.0:0.9, and most preferably to an equimolar ratio of 1:1. Other formaldehyde sources, for example trioxane, have been found to be too unreactive in the inventive process as compared to paraformaldehyde.

The product can be isolated by conventional methods. The isolation is preferably accomplished by distillation, more preferably by fractional distillation.

The process is suitable for preparing all alkyl(methoxymethyl)-trimethylsilanylmethylamines. It is eminently suitable for preparing compounds of the general formula (1) where the various radicals R ($R_1$, $R_2$, etc.) are hydrogen or organic radicals, preferably hydrocarbon or substituted hydrocarbon radicals:

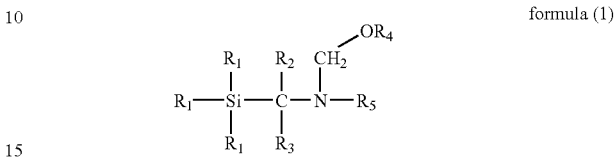

formula (1)

where each of the various radicals are the same or different, and are preferably defined as follows: $R_1$=methyl or ethyl, $R_2$=methyl or hydrogen, $R_3$=methyl or hydrogen, $R_4$=$C_1$-$C_4$ alkyl, $R_5$=$C_1$-$C_{12}$ alkyl, benzyl, tert-butyl, 2-vinylbenzyl, isopropyl, 2-hydroxy-2-phenylethanoyl, 4-nonylbenzyl, 4-chlorobenzyl, 4-bromobenzyl, allyl, 3-pyridylmethyl, (R)-1-phenylethyl, (S)-1-phenylethyl, (S)-1-naphthylethyl and cyclohexyl.

Particular preference is given to the process for preparing compounds of the general formula (I) where $R_1$ and $R_4$ are each defined as methyl, $R_2$ and $R_3$ are each defined as hydrogen, and $R_5$ is selected from the group comprising ethyl, benzyl and tert-butyl.

In the kinetic evaluation of the reactions with aqueous formaldehyde solution known from the prior art by means of differential scanning calorimetry (DSC), DSC analyses showed critical onset temperatures with high decomposition enthalpies. Especially critical is the biphasic reaction mixture after the metered addition of alkyltrimethylsilanylmethylamine and the distillation bottoms after the isolation by distillation. Surprisingly, these problems have been solved by the addition of an equimolar amount of paraformaldehyde to the alkyltrimethylsilanylmethylamine, instead of the aqueous formaldehyde solution as the formaldehyde source.

Compared to the processes with aqueous formaldehyde solution, the process of the invention leads to significantly higher yields and opens up the possibility of isolating the particular target compound by distillation.

It is believed that the higher yields arise principally through the formation of a lower level of by-products in the reaction of paraformaldehyde. For instance, an alkyl(methoxymethoxymethyl)trimethylsilanylmethylamine by-product is observed only in traces in the case of use of paraformaldehyde. In the case of use of an aqueous formaldehyde solution, in contrast, approx. 10 mol % of this compound is formed. The cause of this side reaction lies in the stabilization of the aqueous formaldehyde solution with methanol. The hemiacetal formed from methanol and formaldehyde can attack the hemiaminal formed as an intermediate in an analogous manner in the synthesis of the target compound. Moreover, in the case of use of paraformaldehyde, the dimerization reaction is suppressed (reaction scheme IV).

Reaction scheme IV

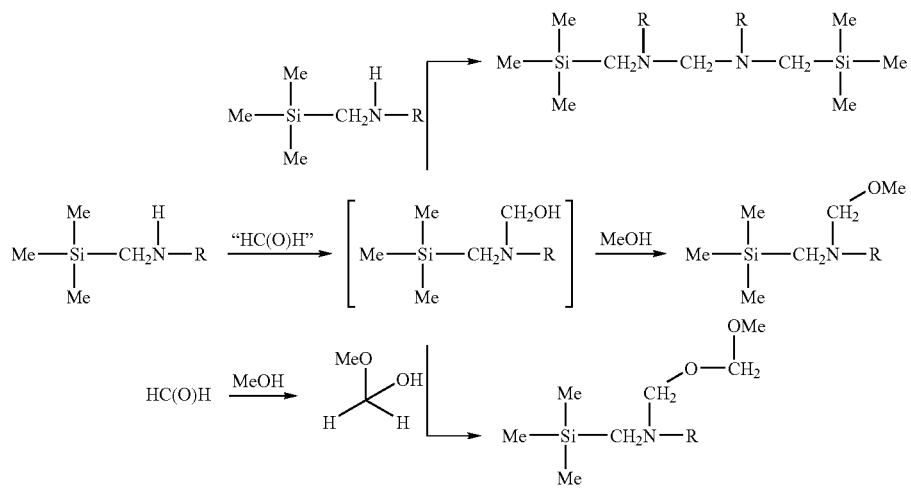

The examples which follow will illustrate the present invention in detail, but should not be construed as limiting the scope of the invention.

EXAMPLE 1

Comparative Example

Synthesis of ethyl(methoxymethyl)trimethylsilanylmethylamine by Reaction Using Aqueous Formaldehyde Solution 18.5 g (0.228 mol) of a 37% aqueous formaldehyde solution are initially charged and cooled to 0° C. At this temperature, 30.0 g (0.175 mol) of ethyltrimethylsilanylmethylamine are metered in within 15 min. Subsequently, at this temperature, within 5 min, 11.1 g (0.346 mol) of methanol and 12.0 g (0.087 mol) of potassium carbonate are metered in. The reaction mixture is stirred at 0° C. for 1 h and then warmed to room temperature. The phases are separated, and the upper organic phase is admixed with 2.0 g (0.014 mol) of potassium carbonate and stirred at room temperature for 1 h. The solid is filtered off and the filtrate is fractionally distilled. Yield 6.30 g (22%) of a colorless liquid. –b.p. 67° C./50 mbar. –$^1$H NMR ($C_6D_6$): δ=0.10 (s, 9 H), 1.70 (t, 3 H), 2.12 (s, 2 H), 2.40 (q, 2 H), 3.18 (s, 3 H), 3.89 (s, 2 H).

DSC Analyses:
  biphasic reaction mixture after the further reaction time (onset temperature: 62° C., decomposition enthalpy 148 J/g)
  distillation bottoms (onset temperature: 107° C., decomposition enthalpy 754 J/g).

EXAMPLE 2

Synthesis of ethyl(methoxymethyl)trimethylsilanylmethylamine (Equimolar Reaction)

18.0 g (0.13 mol) of potassium carbonate, 121.8 g (3.80 mol) of methanol and 60.0 g (2.00 mol) of paraformaldehyde are initially charged and cooled to –5° C. At this temperature, within 30 min, 262.6 g (2.00 mol) of ethyltrimethylsilanylmethylamine are metered in. The biphasic reaction mixture is stirred at –5° C. for a further 1 h and then warmed to room temperature within 20 min. Within 1 min, 382 g of pentane are metered in. The biphasic reaction mixture is separated and the upper, organic phase is dried azeotropically for 2 h. The organic phase is concentrated and then fractionally distilled. Yield 228.5 g (71%) of a colorless liquid.

DSC Analyses:
  biphasic reaction mixture after the further reaction time (onset temperature: 121° C., decomposition enthalpy 360 J/g) (although the exothermicity is higher compared to the old process, the onset temperature is sufficiently high that the 100K rule is complied with)
  distillation bottoms (onset temperature: 121° C., decomposition enthalpy 80 J/g).

EXAMPLE 3

Comparative Example

Synthesis of benzyl(methoxymethyl)trimethylsilanylmethylamine (Reaction with 1.3 eq. of Paraformaldehyde)

2.00 g (0.014 mol) of potassium carbonate, 24.4 g (0.76 mol) of methanol and 15.6 g (0.52 mol) of paraformaldehyde are initially charged and cooled to 0° C. At this temperature, within 30 min, 77.4 g (0.40 mol) of benzyltrimethylsilanylmethylamine are metered in. The biphasic reaction mixture is stirred at 0° C. for a further 1 h and then warmed to room temperature within 20 min. Within 1 min, 190.9 g of pentane are metered in. The biphasic reaction mixture is separated and the upper organic phase is dried azeotropically for 2 h. The organic phase is concentrated and then fractionally distilled. Yield 74.9 g (79%) of a colorless liquid.

DSC Analyses:
  upper layer of the biphasic reaction mixture after the further reaction time (onset temperature: 154° C., decomposition enthalpy 414 J/g)
  lower layer of the biphasic reaction mixture after the further reaction time (onset temperature: 72° C., decomposition enthalpy 123 J/g)

distillation bottoms (onset temperature: 134° C., decomposition enthalpy 461 J/g).

EXAMPLE 4

Synthesis of
benzyl(methoxymethyl)trimethylsilanylmethylamine
(Equimolar Reaction)

2.50 g (0.018 mol) of potassium carbonate, 30.4 g (0.95 mol) of methanol and 15.0 g (0.50 mol) of paraformaldehyde are initially charged and cooled to 0° C. At this temperature, within 30 min, 96.7 g (0.50 mol) of benzyltrimethylsilanylmethylamine are metered in. The biphasic reaction mixture is stirred at 0° C. for a further 1 h and then warmed to room temperature within 20 min. Within 1 min, 190.9 g of pentane are metered in. The biphasic reaction mixture is separated and the upper, organic phase is dried azeotropically for 2 h. The organic phase is concentrated and then fractionally distilled. Yield 105.9 g (89%) of a colorless liquid. –b.p. 94° C./1 mbar. –$^1$H NMR ($C_6D_6$): δ=0.09 (s, 9 H), 2.21 (s, 2 H), 3.00 (s, 3 H), 3.75 (s, 2 H), 3.87 (s, 2 H), 7.10-7.45 (m, 5 H).

DSC Analyses:
- upper layer of the biphasic reaction mixture after the further reaction time (onset temperature: 225° C., decomposition enthalpy 163 J/g)
- lower layer of the biphasic reaction mixture after the further reaction time (onset temperature: 80° C., decomposition enthalpy 14 J/g)
- distillation bottoms (onset temperature: 210° C., decomposition enthalpy 646 J/g).

EXAMPLE 5

Synthesis of
benzyl(methoxymethyl)trimethylsilanylmethylamine
(Reactions with Different Stoichiometries)

The reactions were carried out analogously to Example 4, with the stoichiometries set forth in Table 1. In the inventive process, the stoichiometry is crucial for yield and onset temperature. The decomposition enthalpies reported are based on the distillation bottoms.

TABLE 1

| Experiment | Yield | eq. PFA | Onset 1 | Decomposition enthalpy 1 | Onset 2 | Decomposition enthalpy 2 |
|---|---|---|---|---|---|---|
| 4(a) | 43.8 | 0.90 | 260° C. | 69 J/g | | |
| 4(b) | 66.0 | 0.95 | 256° C. | 400 J/g | | |
| 4(c) | 81.3 | 1.00 | 245° C. | 91 J/g | — | — |
| 4(d) | 81.2 | 1.05 | 158° C. | 291 J/g | 361° C. | 12 J/g |

In the case of substoichiometric use of paraformaldehyde, the yield falls (from 81.3% at 1.0 equivalent to 43.8% at 0.90 equivalent). In the case of superstoichiometric use of paraformaldehyde (1.05 eq.), the yield remains virtually unchanged, but the onset temperature falls from approx. 250° C. to 158° C.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing alkyl(methoxymethyl)trialkylsilanylmethylamines comprising reacting alkyltrialkylsilanylmethylamines with paraformaldehyde and methanol in the presence of a base, in a molar ratio of paraformaldehyde to alkyltrialkylsilanylmethylamine of from 0.8:1.0 to 1.0:0.8, wherein the alkyl groups of the trialkylsilanyl moieties are methyl or ethyl groups.

2. The process of claim 1, wherein paraformaldehyde, methanol and the base used are initially charged at the start of the reaction.

3. The process of claim 1, wherein at least one base is selected from the group consisting of $K_2CO_3$, $Na_2CO_3$, NaOH and NaOMe.

4. The process of claim 1, wherein alkyl(methoxymethyl)trimethylsilanylmethylamine product is isolated by distillation.

5. The process of claim 1, wherein the reaction temperature is in the range between –20° C. and 40° C.

6. The process of claim 1, wherein the ratio of molar equivalents of alkyltrimethylsilanylmethylamine to methanol is between 1.0 and 2.5.

7. A process for preparing alkyl(alkoxymethyl)trialkylsilanylamines, comprising reacting alkyltrialkylsilanylmethylamines with paraformaldehyde and a $C_{1-4}$ alkanol in the presence of base, in a molar ratio of paraformaldehyde to alkyltrialkylsilanylmethylamine of from 0.8:1 to 1.0:0.8 and wherein the alkyl groups of the trialkylsilanyl moieties are methyl or ethyl groups, to form a product of the formula (1)

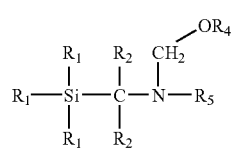

formula (1)

where the radicals are the same or different and are defined as follows: $R_1$=methyl or ethyl, $R_2$=methyl or hydrogen, $R_3$=methyl or hydrogen, $R_4$=$C_1$-$C_4$ alkyl, $R_5$=$C_1$-$C_{12}$ alkyl, benzyl, tert-butyl, 2-vinylbenzyl, iso-propyl, 2-hydroxy-2-phenylethanoyl, 4-nonylbenzyl, 4-chlorobenzyl, 4-bromobenzyl, allyl, 3-pyridylmethyl, (R)-1-phenylethyl, (S)-1-phenylethyl, (S)-1-naphthylethyl or cyclohexyl.

8. The process of claim 7, wherein $R_1$ and $R_4$ are each defined as methyl, $R_2$ and $R_3$ are each defined as hydrogen, and $R_5$ is ethyl, benzyl or tert-butyl.

9. The process of claim 1, wherein the molar ratio of paraformaldehyde to alkyltrimethylsilanylmethylamine is from 0.9:1.0 to 1.0:0.9.

10. The process of claim 1, wherein the molar ratio of paraformaldehyde to alkyltrimethylsilanylmethylamine is about 1:1.

* * * * *

UNITED STATES PATENT AND TRADEMARK OFFICE
CERTIFICATE OF CORRECTION

PATENT NO. : 7,847,117 B2
APPLICATION NO. : 12/180716
DATED : December 7, 2010
INVENTOR(S) : Markus Merget It is certified that error appears in the above-identified patent and that said Letters Patent is hereby corrected as shown below:

Column 8, Line 35, Claim 7:
Delete:

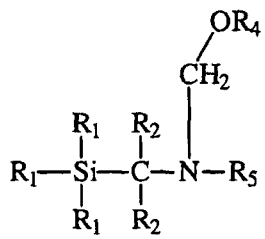

" Formula 1 "

and Insert:

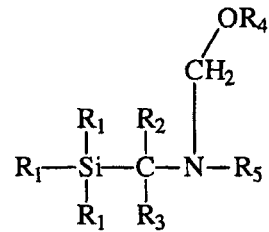

-- Formula 1 --

Signed and Sealed this
Twenty-second Day of February, 2011

David J. Kappos
*Director of the United States Patent and Trademark Office*